(12) United States Patent
Kerem et al.

(10) Patent No.: US 11,369,315 B2
(45) Date of Patent: Jun. 28, 2022

(54) MULTIFUNCTIONAL PERSONAL HEALTH MONITOR WITH AN ACTIVITY TRACKER EMBEDDED INTO A PET LEASH

(71) Applicants: Samuel Kerem, Rockville, MD (US); Michaela Polina Kerem, Rockville, MD (US)

(72) Inventors: Samuel Kerem, Rockville, MD (US); Michaela Polina Kerem, Rockville, MD (US)

( * ) Notice: Subject to any disclaimer, the term of this patent is extended or adjusted under 35 U.S.C. 154(b) by 1093 days.

(21) Appl. No.: 15/633,628

(22) Filed: Jun. 26, 2017

(65) Prior Publication Data

US 2018/0368776 A1 Dec. 27, 2018

(51) Int. Cl.
*A61B 5/00* (2006.01)
*A01K 27/00* (2006.01)
(Continued)

(52) U.S. Cl.
CPC .......... *A61B 5/6887* (2013.01); *A01K 27/004* (2013.01); *A61B 5/0022* (2013.01); *A61B 5/0028* (2013.01); *A61B 5/0077* (2013.01); *A61B 5/02055* (2013.01); *A61B 5/1112* (2013.01); *A61B 5/1118* (2013.01); *A61B 5/282* (2021.01); *G01S 19/13* (2013.01);
(Continued)

(58) Field of Classification Search
CPC ..... A01K 27/004; A01K 27/00–27/009; A61B 5/6887; A61B 5/282; A61B 5/0022; A61B 5/0028; A61B 5/0077; A61B 5/02055; A61B 5/1112; A61B 5/1118; A61B 5/01; A61B 5/0205; A61B 5/7246; A61B 5/74; A61B 5/7435; A61B 5/747; A61B 2560/0214; A61B 2562/0219; A61B 2562/0247; A61B 2562/04; G01S 19/13; G08B 21/0453; G08B 21/0461; G08B 25/016; H02J 50/00; H02J 7/025; H02J 7/14
See application file for complete search history.

(56) References Cited

U.S. PATENT DOCUMENTS 4,707,685 A * 11/1987 Carrier ................. A61D 17/008
340/539.1
8,679,012 B1 * 3/2014 Kayyali ................. A61B 5/318
600/301

(Continued)

OTHER PUBLICATIONS

Amazon, Petkit 'Go' Bluetooth USB Charging Route and Walk Distance Tracking Activity Monitor Smart Pet Dog Leash w/ User Controlled Light Sensors; Date First Available: Oct. 30, 2017; https://www.amazon.com/PETKIT-Bluetooth-Charging-Distance-Controlled/dp/B076ZQ57ZS (Year: 2017).*

(Continued)

*Primary Examiner* — Jonathan T Kuo

(57) ABSTRACT

A multifunctional personal health monitor with an activity tracker embedded into a pet leash is provided. The energy of a pet pulling the leash cord is converted to an electrical power to run and to analyze operation of multiple biometric sensors embedded into the leash. The physical activities of the pet and its owner may be tracked. The obtain biometric information may be wirelessly transmitted for additional processing or an emergency call can be initiated. The generated by pet movement electrical power may be used to charge various external devices.

13 Claims, 4 Drawing Sheets

(51) Int. Cl.
*A61B 5/11* (2006.01)
*A61B 5/0205* (2006.01)
*G01S 19/13* (2010.01)
*G08B 25/01* (2006.01)
*G08B 21/04* (2006.01)
*A61B 5/282* (2021.01)
*A61B 5/01* (2006.01)
*H02J 50/00* (2016.01)
*H02J 7/14* (2006.01)
*H02J 7/02* (2016.01)

(52) U.S. Cl.
CPC ..... *G08B 21/0453* (2013.01); *G08B 21/0461* (2013.01); *G08B 25/016* (2013.01); *A61B 5/01* (2013.01); *A61B 5/0205* (2013.01); *A61B 5/7246* (2013.01); *A61B 5/74* (2013.01); *A61B 5/747* (2013.01); *A61B 5/7435* (2013.01); *A61B 2560/0214* (2013.01); *A61B 2562/0219* (2013.01); *A61B 2562/0247* (2013.01); *A61B 2562/04* (2013.01); *H02J 7/025* (2013.01); *H02J 7/14* (2013.01); *H02J 50/00* (2016.02)

(56) References Cited

U.S. PATENT DOCUMENTS

| | | | | |
|---|---|---|---|---|
| 9,224,096 | B2* | 12/2015 | Oppenheimer | G06N 5/02 |
| 10,750,721 | B2* | 8/2020 | Morin | H02J 50/10 |
| 2008/0173257 | A1* | 7/2008 | Steiner | A01K 27/004 |
| | | | | 119/796 |
| 2008/0223308 | A1* | 9/2008 | Stern | A01K 27/004 |
| | | | | 119/720 |
| 2011/0126778 | A1* | 6/2011 | Mitchell | A01K 27/004 |
| | | | | 119/796 |
| 2014/0089243 | A1* | 3/2014 | Oppenheimer | G08B 21/0275 |
| | | | | 706/46 |
| 2015/0282456 | A1* | 10/2015 | Harley | A01K 27/006 |
| | | | | 119/796 |
| 2016/0050890 | A1* | 2/2016 | Fitzgerald | A01K 27/003 |
| | | | | 119/795 |
| 2017/0172462 | A1* | 6/2017 | Alghazi | A45B 5/00 |
| 2020/0085018 | A1* | 3/2020 | Morin | H02J 7/0042 |

OTHER PUBLICATIONS

Amazon, PETKIT Smart Dog Leash with Ultra Comfortable Grip, Led Light System, Lock & Release Mechanism, 4ft Replaceable Leash with Hook, Dog Walking Leash; Date First Available: Feb. 16, 2017; https://www.amazon.com/PETKIT-Comfortable-Release-Mechanism-Replaceable/dp/B06X1BHNMH (Year: 2017).*

Wikipedia, Pulse oximetry, May 6, 2016, http://web.archive.org/web/20160506111441/https://en.wikipedia.org/wiki/Pulse_oximetry (Year: 2016).*

* cited by examiner

MULTIFUNCTIONAL PERSONAL HEALTH MONITOR WITH AN ACTIVITY TRACKER EMBEDDED INTO A PET LEASH

CROSS REFERENCES TO RELATED APPLICATIONS

This application claims the benefit of Applicants' prior Provisional Application No. 62/354,748 filed on Jun. 25, 2016.

BACKGROUND

Growing consumer interest in personal health has led to a variety of personal health monitoring devices being offered on the market. Such devices were typically designed to cover a limited number of monitoring features. Recent advances in sensor, electronics, and power source miniaturization have brought to the market new generation of personal health monitoring devices referred herein also as biometric monitoring devices. Currently, available personal health and activity monitors are worn on a wrist and thus have to be made small. The small size of the device restricts the size of an internal battery thus limiting the amount of available electrical power and time duration to acquire and to process the biometric signals. Ironically, the main limiting factor for the personal health monitors or activity trackers is not the processing power of the internal processor, but the minuscule amount of electrical power stored inside such devices. The operational time of such devices is inversely proportional to the power drained from the battery, so the device operation is forced to low power or sleep mode most of the time. The wrist-based health monitor shifts during normal physical activity thus making signal acquisition not reliable. The finite stored energy and a small size of the wrist-worn devices limit the number of embedded sensors and limit the scope of biometric monitoring mainly to a heart or pulse rate. To acquire a more delicate signal, such as Electrocardiogram, the physical connection between the electrodes of the device and a user's skin must be tight and reliable, which is impossible for loosely worn an armband-based personal health monitor. Emerging more advanced health monitoring devices, such as non-invasive glucose level monitors consume at least order of magnitude more power than current heart and pulse monitors, making operational time of a device based solely on a rechargeable internal battery non-practical.

SUMMARY

The present invention is related to a handheld biometric monitoring device that is placed into a retractable pet leash. The leash housed generator converts the kinetic energy of a pet into an electrical power; the electrical energy is stored to support continuous operation of a plurality of biometric sensors, to process, record and transmit multiple biometric signals, and to power external devices through a connector and by wireless power transfer. The biometric sensors are placed into the leash handle with the holder's grip providing reliable signal interaction with the sensors. The surface area and the volume of the leash allow placement of multiple communication modules and biometric sensors with multi-functional variety. Multiple types of wireless communication, user interfaces such as a microphone, display, GPS accelerometer to detect falling and emergency button allow to track activity and location through a constantly present cellular connection and to make an outreach call in an emergency situation.

BRIEF DESCRIPTION OF THE DRAWINGS

Various embodiments of the invention are disclosed in the following detailed description and accompanying drawings.

DETAILED DESCRIPTION AND PREFERRED EMBODIMENT

The following is a detailed description of exemplary embodiments to illustrate the principles of the invention. The embodiments are provided to illustrate aspects of the invention, but the invention is not limited to any embodiment. The scope of the invention encompasses numerous alternatives, modifications and equivalent; it is limited only by the claims.

Numerous specific details are set forth in the following description in order to provide a thorough understanding of the invention. However, the invention may be practiced according to the claims without some or all of these specific details. For the purpose of clarity, technical material that is known in the technical fields related to the invention has not been described in detail so that the invention is not unnecessarily obscured.

Recent developments in electronics make possible to create very powerful data and signal processors that occupy very little space. Ironically, it is not an internal processor data acquisition and processing power put a limit on personal health monitor capabilities but the finite and small amount of stored electrical energy needed for the device operation. A small physical area of such devices restricts an introduction of a new variety of biometric sensors, communication means, and health and safety features. The invention demonstrates how embedding a health monitor and activity tracker into a retractable pet leash allows building devices with functionality not being limited by a power drain while expanding to a variety of new features. Converting a kinetic energy of a pet, restrained by a retractable leash and utilizing the natural dimensions of the leash allows building a different generation of health monitors and activity trackers that are not limited by the described above hurdles.

Figure 1:
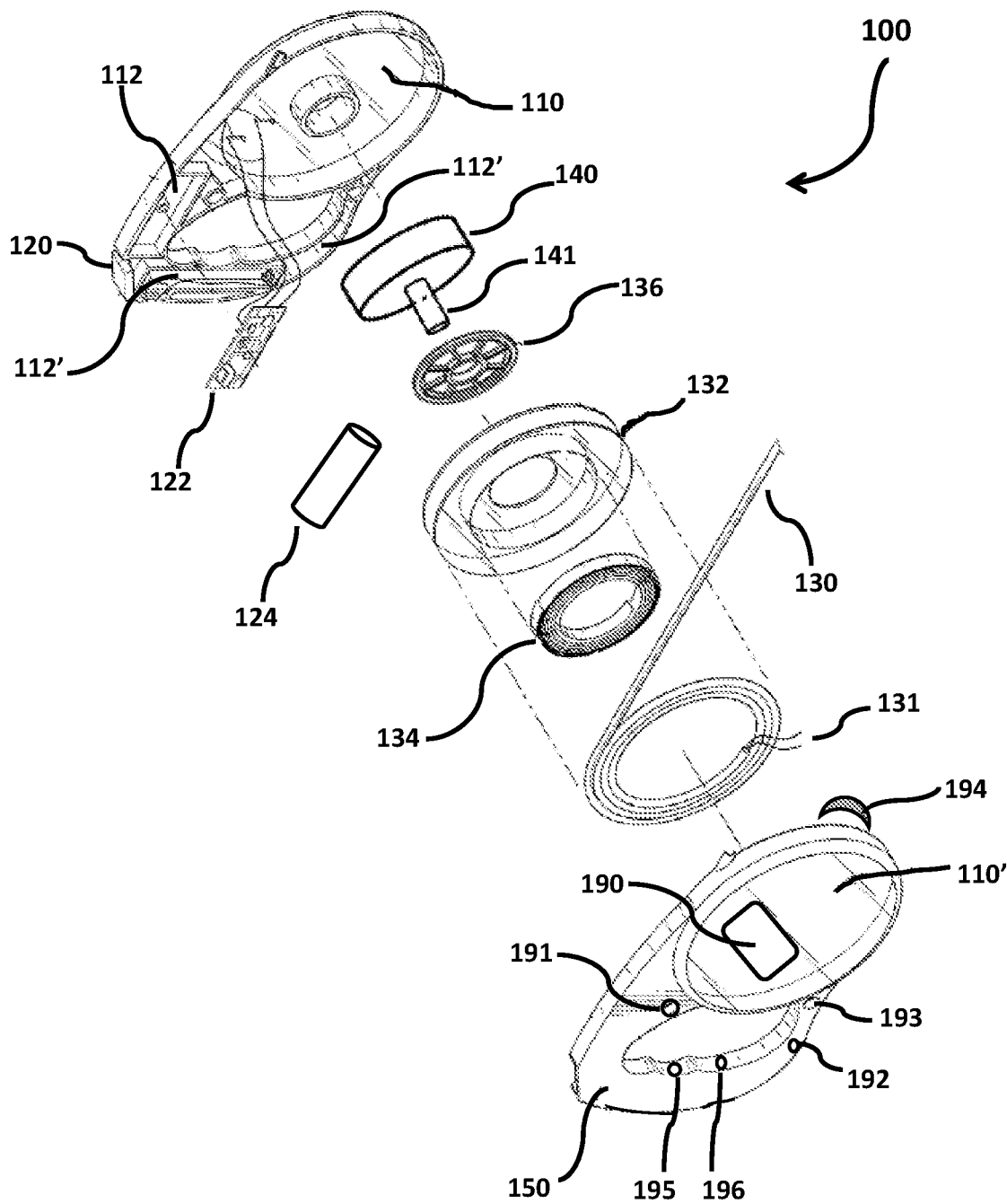
FIG. 1 illustrates an exploded view of the multifunctional personal health monitor with an activity tracker embedded into a pet leash.

One embodiment of a health monitor device is shown in FIG. 1. Health monitor device container 100 consists of the container's two halves 110 and 110'. The device container holds few compartments 112, 112', and 112" to keep various operational modules, such as: sensor acquisition and processing module, data communication module, power conversion and storage module.

The device container houses leash cord 130; the cord is winded on spool 132. If the cord is not pulled out by external force, coil spring 134 rewinds leash cord 130 to spool 132.

A roaming pet attached to leash cord 130 and a free-will individual holding handle 150 create the dynamic system with leash cord 130 being pulled by the animal and retracted by coil spring 134, thus constantly rotating spool 132, thus winding and unwinding leash cord 130 to spool 132. As long as a distance between a person holding health monitor device container 100 and a pet attached to leash cord 130 is changing, an electrical power is being generated and passed to energy storage element 124.

The device container also houses electrical generator 140. Generator 140 comprises of a rotor and a stator, an electrical power is generated while the rotor moves against the stator. Shaft 141 of generator 140 is mechanically attached through joint coupler 136 to spool 132. A fixed mechanical attachment, a V-belt or any type of a motion coupler capable to transfer movement from one mechanical part to another mechanical part can be used as joint coupler 136. Based on such or similar arrangements, spool 132 transfers rotational motion to shaft 141 attached to a rotor of electrical generator 140. Electrical generator 140 converts kinetic energy of leash cord 130 to electrical energy. That energy is stored in energy storage element 124. Some examples of such energy storage element are: a capacitor, a rechargeable battery, a fuel cell.

Energy storage element 124 supplies electrical power to signal and data processor 122. Signal and data processor 122 communicates with plurality of user's interfaces such as: touch sensitive display 190, microphone 191, speakerphone 192, video camera 193, emergency pushbutton 194. Two biometric sensors 195 and 196 are shown for this embodiment and are placed on the surface of handle 150. The sensors can be picked from the plurality of biometric sensors shown on FIG. 2. As an example, biometric Sensors 195 can be implemented as an optical transmitter and receiver pair and biometric sensor 196 can be implemented as Galvanic Skin Response. Or, pair of biometric sensors 230 can be implemented as Electro Cardiogram electrode. An individual who holds health monitor device 100 has a firm grip on handle 150 providing reliable contact between the individual hand and sensors which are placed on handle 150. Contrarily biological signal monitor, from prior art such as FitBit, is worn loosely on a wrist, resulting in not accurate pulse reading and rendering electrocardiogram acquisition as impossible task.

This embodiment also shows connector 120 to transfer electrical power from and data outside. Connector 120 is used to recharge outside devices by getting power from energy storage element 124 and data communicating between processor module 122 and external devices. Possible implementation of such connector is USB or Lightning connector.

Leash cord may comprise flexible conductive wire 131. Conductive wire 131 is used as antenna to enhance communication between multifunctional personal health monitor and external devices.

If a necessity arises emergency pushbutton 194 can initiate cellular call or data transmission. By its nature pet walkers can wander into a remote area with sparse population in such cases fast emergency communication initiated by emergency pushbutton 194 and communication enhanced by antenna implemented as elongated embedded wire 131 can be appreciated.

Figure 2:
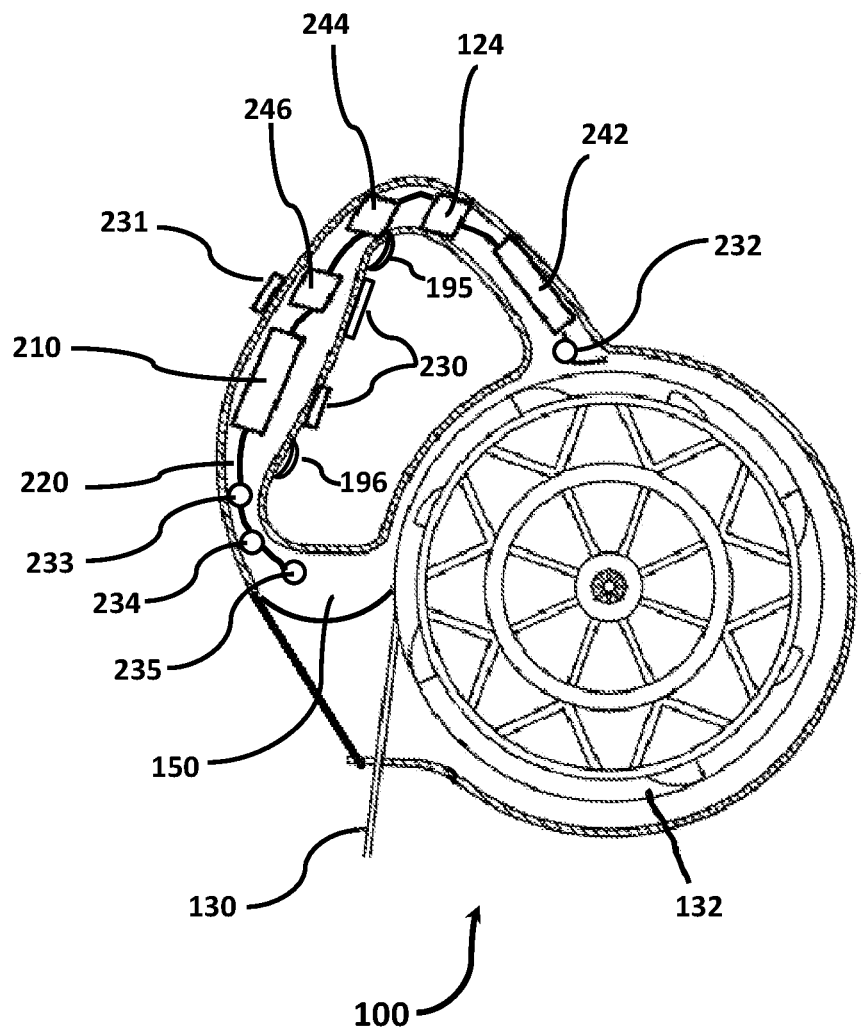
FIG. 2 shows an example of sensor plurality comprised by the device housing.

FIG. 2. Demonstrates possible arrangement and an assortment of plurality biometric sensors and electronic modules comprised by another embodiment of multifunctional personal health monitor and activity tracker.

In comparison to wristband worn monitor, an internal housing of a pet leash naturally meant to store a long leash cord, provides much larger volume and surface area. Access to continuously generated power supports operation of a plurality of sensors and electronic accessories. An access to greater amount of available electrical power permits Bluetooth, Wi-Fi and cellular communication, lifting restriction on the distance between the transmitter and the receiver. A multifunctional personal health monitor may employ one or more power demanding, constantly operational biosensors, placed either inside a device or on the device surface. In addition to optical transmitter receiver pair 195 and galvanic skin response 196, biometric sensors may be chosen from the following plurality: a set of electrocardiogram electrodes 230, electromagnetic transmitter-receiver for under skin penetration 231, capacitive sensor 232, glucose meter 233, ph-meter 234, accelerometer 235. The signal from plurality of biometric sensors is acquired by front-end signal and data processing module 210. Front-end signal processing module 210 is further depicted on FIG. 4. Operation of all electronic modules and sensors is supported by data and power harness 220 that connects all internal modules and components which are dependent on electrical power and data exchange. Front-end signal and data processing module 210 can be a part of signal and data processor 122.

Additional set of electronic modules may augment operation of biometric sensors. These electronic modules may include but not limited to: GPS or Global Positioning System 242, module combining various wireless communication 244. Possible but not all approaches for wireless communication are: cellular, WiFi, Bluetooth, ANT, broadcast radio. Power conversion module 246 provides power for any internal component that requires power. Also, power conversion module 246 brings power to connector 120 to charge external devices if needed. Also, power conversion module 246 brings power to embedded wire 131, to wirelessly transmit power and data.

Figure 3:
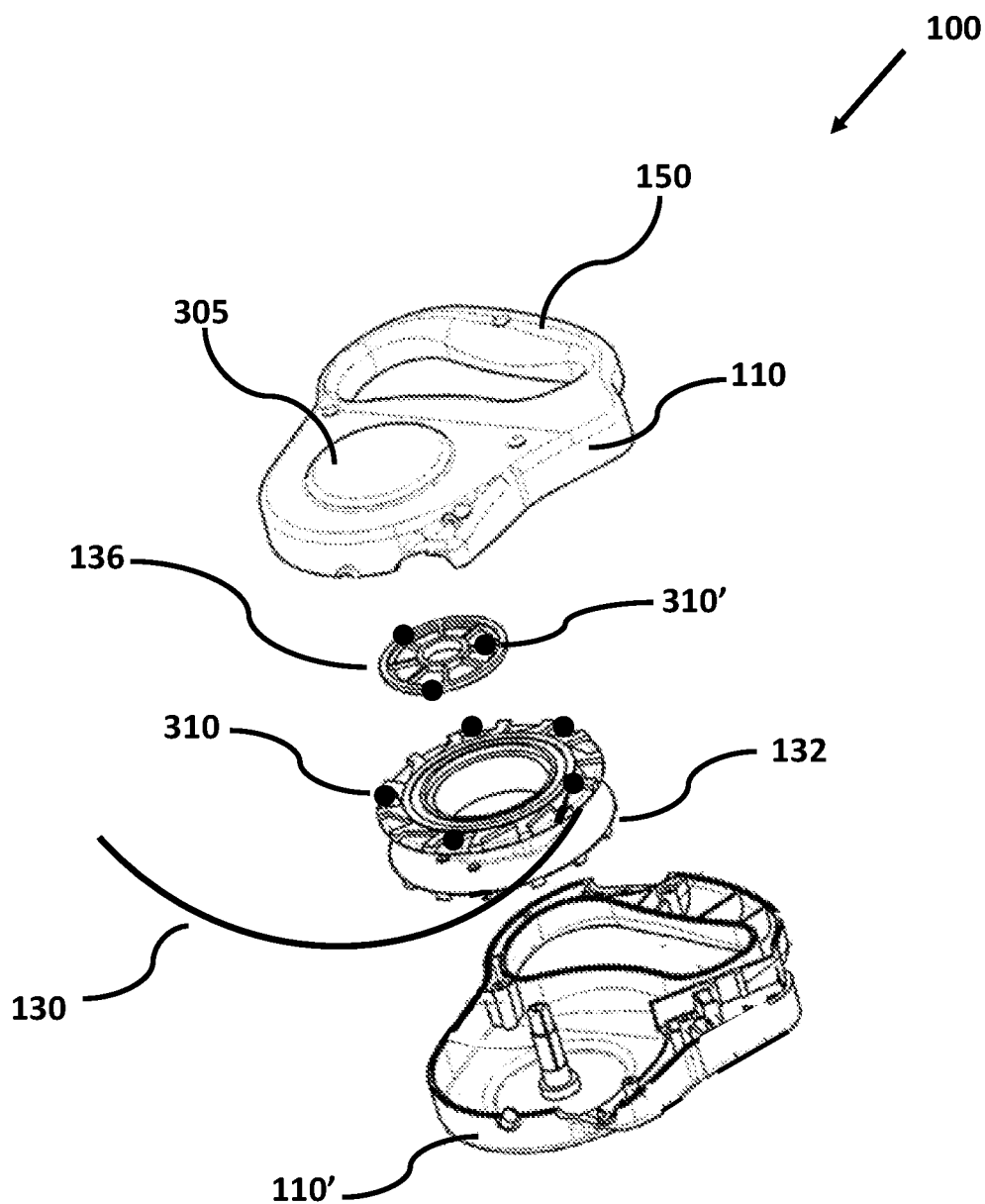
FIG. 3 illustrates another embodiment of power generation for multifunctional health monitor embedded into a pet leash.

FIG. 3 shows a preferred embodiment of health monitor apparatus embedded into a pet leash. On FIG. 3. only power generation section of the apparatus is shown. Instead of having a distinctive electrical generator 140 as it is shown on FIG. 1., the electrical generator is built by embedding its parts into parts of a leash. For one example, permanent magnets 310 and 310' are embedded into rotational parts of the apparatus such as joint coupler 136 or into spool 132. With that approach, shaft 141 can be eliminated and spool 136 itself becoming a rotor of generator 140. Internal conductive windings or coils 305 convert magnetic field movement from permanent magnets 310 and 310' into electrical energy to be stored in energy storage element 124.

Figure 4:
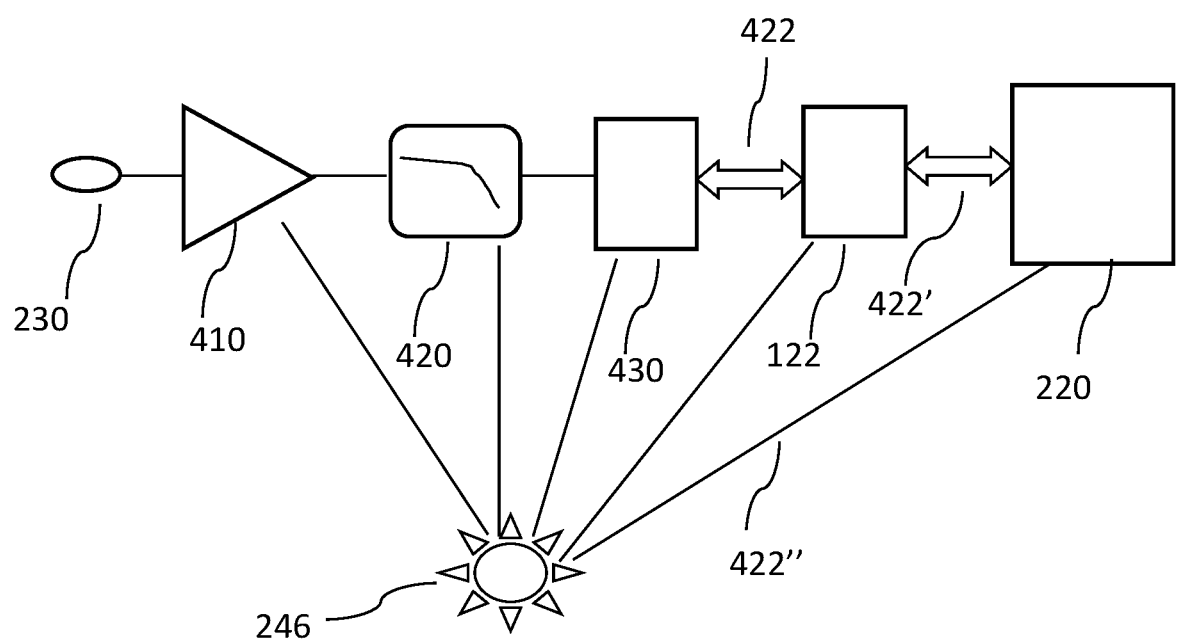
FIG. 4 illustrates possible embodiment of an electronic module, biometric signal acquisition and processing chain.

FIG. 4 shows embodiment of front end signal and data processing module. Electrocardiogram electrode 230 is used as an example of biometric sensor to demonstrate operation of front-end signal and data processing module 210. A signal from biometric sensor is acquired and amplified by amplifier 410. The signal is passed to frequency conversion module 420 that increase signal-to-noise ratio by attenuating frequency components outside of biosensor signal bandwidth. Then signal from frequency conversion module 420 is passed to Analog-to-Digital Converter 430 that converts signal that was originated by electrocardiogram electrode 230 to digital data suitable for processor 122. Signal and data processor 122, through mutually acceptable protocol 422, controls data exchange between itself, Analog-to-Digital converter 430 and all electronic modules. Such mutually acceptable protocols can be but not limited to: 1-Wire interface, I2C interface, SPI interface, parallel interface. Communication bus of mutually acceptable protocols 422 is delivered through data and power harness 220. In addition, signal and data processor 122 monitors energy storage element 246 in order to measure through time the amount and profile of generated electrical power. Because the amount of the generated energy correlates with a behavior of an individual holding the device handle 150 and a behavior of a pet attached to the device leash cord 130, the information of the pet activity can be deduced.

Thus, a Multifunctional Personal Health Monitor with an Activity Tracker Embedded into a Pet Leash has been described. While various embodiments have been described herein, it should be understood that they have been presented by way of example only, and not limitation. It will thus be appreciated that those skilled in the art will be able to devise numerous systems and methods which, although not explicitly shown or described herein, embody said principles of the invention and are thus within the spirit and scope of the invention as defined by the following claims.

What is claimed is:

1. A multifunctional health monitor comprising:
   a pet leash with a retractable cord;
   a pet leash case with an opening for passing the retractable cord;
   a spool for storing said retractable cord;
   a signal and data processing mounted inside the pet leash case;
   an electrical generator and a rechargeable power storage element mounted inside said pet leash case;
   the spool mechanically coupled with a rotor of the electrical generator;
   means for said electrical generator to produce and to deliver generated electrical power to the rechargeable power storage element;
   means for supplying the electrical power from the rechargeable power storage element to the signal and data processor;
   at least one biometric sensor mounted inside said pet leash case or on the surface of said pet leash case;
   means for communication between said signal and data processor and said at least one biometric sensor,
   whereby the electrical generator converts the kinetic energy of a moving pet, connected to the retractable cord, to electrical energy that powers the signal and data processor for processing the at least one biometric sensor's data acquired from a person holding said pet leash;
   whereas said retractable cord is embedded with a conductive material comprising:
   means for the retractable cord to wirelessly transmit and receive radio frequency signals and to wirelessly transmit electrical power.

2. The multifunctional health monitor according to claim 1 whereas the at least one biometric sensor is selected from the group consisting of:
   a biometric sensor for converting physical properties of light into electrical signals;
   a biometric sensor for converting physical properties of mechanical pressure into electrical signals;
   a biometric sensor for converting physical properties of mechanical displacements into electrical signals;
   a biometric sensor for converting physical properties of an electromagnetic field into electrical signals;
   a biometric sensor for converting temperature into an electrical signal;
   a biometric sensor for converting physical properties of acceleration into an electrical signal;
   a biometric sensor for converting galvanic skin response of a human body into an electrical signal;
   a biometric sensor for converting capacitance variations of a human body into electrical signals;
   a biometric sensor for converting resistance variations of a human body into electrical signals;
   a biometric sensor comprising at least one pair of an electromagnetic frequency transmitter and an electromagnetic frequency receiver for under skin penetration of the person holding said pet leash; and
   a biometric sensor comprising at least one pair of an acoustic frequency transmitter and an acoustic frequency receiver for under skin penetration of the person holding said pet leash; and combinations thereof.

3. The multifunctional health monitor according to claim 1, further comprising a data and power harness; and
   at least one internal electronic module and component;
   wherein the signal and data processor is configured to communicate with the at least one biometric sensor and the at least one internal electronic module and component using the data and power harness.

4. The multifunctional health monitor according to the claim 1 comprising:
   at least one wireless communication module; and
   means for said signal and data processor to communicate with said at least one wireless communication module.

5. The multifunctional health monitor according to the claim 1,
   comprising a Global Positioning System; and
   means for said signal and data processor to exchange data with said Global Positioning System.

6. The multifunctional health monitor according to claim 5 comprising:
   the signal and data processor configured to record activity for the person holding said pet leash based on data acquired from the at least one biometric sensor and the Global Positioning System.

7. The multifunctional health monitor according to the claim 1 comprising:
   a microphone, a speakerphone, a touch-sensitive display, and a camera;
   means for said signal and data processor to communicate with the microphone, the speakerphone, the touch-sensitive display, and the camera.

8. The multifunctional health monitor according to claim 1 comprising:
   a pushbutton;
   means for said signal and data processor to communicate with the pushbutton.

9. The multifunctional health monitor according to claim 1 comprising:
   means for said signal and data processor to monitor an amount of power delivered from the electrical generator to the rechargeable power storage element.

10. The multifunctional health monitor according to claim 1 comprising:
    a power and data connector;
    means for connecting said rechargeable power storage element and said signal and data processor to monitor and distribute electrical power and acquired data to an external device.

11. The multifunctional health monitor according to claim 1 whereas said spool is comprised of magnetically permeable materials.

12. The multifunctional health monitor according to claim 1 whereas the electrical generator comprises conductive windings embedded into the pet leash container;
    the conductive windings configured to convert magnetic field movement into the electrical energy.

13. The multifunctional health monitor according to claim 1 comprising:
the signal and data processor configured to record the moving pet's activity based on data acquired from the rechargeable power storage element.

\* \* \* \* \*